United States Patent
Battermann et al.

(10) Patent No.: US 10,959,927 B2
(45) Date of Patent: Mar. 30, 2021

(54) HAIR CONDITIONING SPRAY TREATMENT

(71) Applicant: Henkel AG & Co. KGaA, Duesseldorf (DE)

(72) Inventors: Marlene Battermann, Asendorf (DE); Sylvia Kerl, Boenningstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/695,783

(22) Filed: Nov. 26, 2019

(65) Prior Publication Data
US 2020/0188255 A1 Jun. 18, 2020

(30) Foreign Application Priority Data
Dec. 17, 2018 (DE) .................. 10 2018 221 973.7

(51) Int. Cl.
*A61K 8/362* (2006.01)
*A61K 8/42* (2006.01)
*A61K 8/73* (2006.01)
*A61Q 5/12* (2006.01)

(52) U.S. Cl.
CPC ............... *A61K 8/362* (2013.01); *A61K 8/42* (2013.01); *A61K 8/737* (2013.01); *A61Q 5/12* (2013.01)

(58) Field of Classification Search
CPC .......... A61K 8/362; A61K 8/42; A61K 8/737; A61Q 5/12
See application file for complete search history.

(56) References Cited

U.S. PATENT DOCUMENTS 5,833,999 A * 11/1998 Trinh .................. A61K 8/02
424/401
2018/0116930 A1 * 5/2018 Degeorge ............... A61Q 5/065
2018/0140531 A1 * 5/2018 Singer .................... A61K 8/19

FOREIGN PATENT DOCUMENTS

GB  2572481 A  10/2019
WO  2019191747 A1  10/2019

OTHER PUBLICATIONS

Ajinomoto, "New Hair Care Ingredients", Dec. 1, 2016, retrieved from https://www.happi.com/issues/2016-12-01/view_features/new-hair-care-ingredients on Sep. 1, 2020. (Year: 2016).*
BASF, "Dehyquart F 75", Nov. 26, 2013. (Year: 2013).*
Anjana, "Ingredients to look for in a Conditioner", Oct. 31, 2017, retrieved from https://www.curlsandbeautydiary.com/ingredients-look-conditioner on Sep. 1, 2020. (Year: 2017).*
Internet Citation—"Natural revival hair conditioner", dated May 12, 2014 retrieved from the Internet: https://es.siberianhealth.com/en/catalog/product/401823/.

* cited by examiner

*Primary Examiner* — Jianfeng Song
(74) *Attorney, Agent, or Firm* — Lorenz & Kopf, LLP

(57) ABSTRACT

The present disclosure relates to hair conditioning spray treatments comprising at least two components selected from: at least one cationic guar derivative, at least one dicarboxylic acid, or a salt or derivative thereof, and at least one cationic surfactant selected from an amidoamine, a permanent cationic amidoamine, and mixtures thereof. The present disclosure also relates to methods of conditioning hair using the hair conditioning spray treatments.

1 Claim, No Drawings

HAIR CONDITIONING SPRAY TREATMENT

CROSS-REFERENCE TO RELATED APPLICATION

This application claims priority to German Patent Application No. 10 2018 221 973.7, filed Dec. 17, 2018, which is incorporated herein by reference in its entirety.

TECHNICAL FIELD

The present disclosure generally relates to hair care compositions, and more particularly relates to a hair conditioning spray treatment comprising at least two components selected from cationic guar derivatives, dicarboxylic acids (or salts or derivatives thereof), and cationic surfactants. The treatments are preferably free of silicones. The present disclosure also relates to the use of the treatments for the care of keratinous fibers.

BACKGROUND

Hair care compositions are used to style, cleanse and provide a pleasant feel to the hair. Such compositions come in a variety of forms, and include shampoos, conditioners, leave-on conditioning sprays and styling products.

Some hair care compositions, such as conditioners, are used to moisturize and condition the hair, to restore some of the moisture that was removed by a cleansing or shampoo composition. Such compositions may include conditioning agents, which act to retain moisture in the hair by a variety of mechanisms. Some conditioning agents, such as dimethicone, form a barrier and act to prevent the evaporation of moisture from the hair. Other agents, such as propylene glycol, act as humectants to attract moisture to the hair. In each case, the benefit persists only as long as the benefit agent is present on the hair. As such, providing an encapsulated benefit agent may provide increased benefits to hair feel and appearance by providing an extended release of the benefit agent by continuing to deposit the benefit agent onto the hair as the hair is touched, combed, brushed, or otherwise manipulated.

Additional hair care compositions are leave-in compositions. These include styling gels, hairsprays, creams, pomades, or waxes. Such compositions may also include benefit agents, such as moisturizing ingredients, conditioning ingredients, and illuminating ingredients. These benefit agents act immediately upon contact with the hair but may decrease in efficacy over time. As a result, providing an encapsulated benefit agent may assist the benefit agent to provide increased benefit to hair feel and appearance by providing a gradual deposit of the benefit agent onto the hair as the hair is physically manipulated and the capsules are opened, releasing the benefit agent onto the hair.

In addition to the natural environmental influences, human hair is exposed to a number of other, in particular cosmetic, stresses. To these, the strains include, for example, the coloring of the hair and its deformation, for example by a perm. To reduce the adverse effects of the hair structure affecting (environmental) influences, but also to maintain and improve the natural hair structure cosmetic hair products are used. An essential active ingredient in many of these cosmetics are the organosilicon compounds, in particular the silicones such as trisiloxanes, which are exemplified by nourishing properties. The disadvantages of these silicones are the reduced penetration of active ingredients and auxiliaries into the hair due to wetting of the hair surface and the hair styling being hampered by the wetting of the hair surface. Further, due to their persistence in the environment, it is preferable to dispense with the use of cyclomethicones.

The provision of low-silicone or silicone-free care products is therefore a relevant task in the field of hair cosmetics. However, silicone-free leave-on products do not always exhibit the same caring properties as silicone-based products, and it is a challenge to formulate cosmetically acceptable formulations at the care levels of silicones, without using silicones.

Accordingly, it is desirable to provide a hair conditioning treatment that is silicone-free and that has enhanced care properties. Furthermore, other desirable features and characteristics will become apparent from the subsequent detailed description and the appended claims, taken in conjunction with the foregoing technical field and background.

BRIEF SUMMARY

Accordingly, hair conditioning spray treatments and methods for conditioning hair using the hair conditioning spray treatments are provided. In accordance with an exemplary embodiment, a hair conditioning spray treatment is provided comprising at least two components selected from components (i), (ii) and (iii):
 (i) at least one cationic guar derivative,
 (ii) at least one dicarboxylic acid, or a salt or derivative thereof, and
 (iii) at least one cationic surfactant selected from an amidoamine, a permanent cationic amidoamine, and mixtures thereof.

In accordance with another exemplary embodiment, a hair conditioning spray treatment is provided. The hair conditioning spray treatment comprises guar hydroxypropyltrimonium chloride, succinic acid, and brassicamidopropyl dimethylamine or succinic acid, brassicamidopropyl dimethylamine and bis-(isostearoyl/oleoyl isopropyl) dimonium methosulfate.

In accordance with a further exemplary embodiment, a method of conditioning keratin fibers is provided. The method comprises the steps of: contacting a keratin fiber with a conditioning-effective amount of a hair conditioning spray treatment comprising at least two components selected from components (i), (ii) and (iii):
 (i) at least one cationic guar derivative,
 (ii) at least one dicarboxylic acid, or a salt or derivative thereof, and
 (iii) at least one cationic surfactant selected from an amidoamine, a permanent cationic amidoamine, and mixtures thereof.

DETAILED DESCRIPTION

The following detailed description of the present disclosure is merely exemplary in nature and is not intended to limit the present disclosure or the application and uses of the present disclosure. Furthermore, there is no intention to be bound by any theory presented in the preceding background of the present disclosure or the following detailed description of the present disclosure.

The inventors have surprisingly found that the care performance of a silicone-free spray treatment is significantly improved by incorporating therein a combination of at least two components selected from components (i), (ii) and (iii):
 (i) at least one cationic guar derivative (ii) at least one dicarboxylic acid, or a salt or derivative thereof, and (iii) at least one cationic surfactant selected from an amidoamine, a permanent cationic amidoamine, and mixtures thereof.

The combination of brassicamidopropyl dimethylamine, succinic acid and guar hydroxypropyltrimonium chloride was particularly shown to achieve the beneficial care levels, especially compared to a commercially available leave-on silicone oil-based formulation.

In an exemplary embodiment, the hair conditioning spray treatment comprises at least one cationic guar derivative, and at least one dicarboxylic acid, or a salt or derivative thereof.

In another exemplary embodiment, the hair conditioning spray treatment comprises at least one cationic guar derivative, and at least one cationic surfactant selected from an amidoamine, a permanent cationic amidoamine, and mixtures thereof.

In a further exemplary embodiment, the hair conditioning spray treatment comprises at least one dicarboxylic acid, or a salt or derivative thereof, and at least one cationic surfactant selected from an amidoamine, a permanent cationic amidoamine, and mixtures thereof.

In an exemplary embodiment, the hair conditioning spray treatment comprises at least one cationic guar derivative, and at least one dicarboxylic acid, or a salt or derivative thereof, and at least one cationic surfactant selected from an amidoamine, a permanent cationic amidoamine, and mixtures thereof.

Further details as to options for the components are disclosed herein.

In an exemplary embodiment, compositions contemplated herein are provided in the form of a spray. The spray may also contain additional components, such as fragrances to provide the user with a sensory awareness that the benefit agent has been released.

There is also provided a method of conditioning keratin fibers, the method comprising contacting a keratin fiber with a conditioning-effective amount of the hair conditioning spray treatment disclosed herein, in accordance with an exemplary embodiment.

There is also provided a method of conditioning keratin fibers, comprising contacting a plurality of keratin fibers with an amount of the hair conditioning spray treatment as disclosed herein effective to increase the volume of the keratin fibers on styling, in accordance with an exemplary embodiment.

There is also provided a method for conditioning keratin fibers, wherein the hair conditioning spray treatment as disclosed herein is spray-applied onto wet or dry keratin fibers and left on the keratin fibers until they are next washed, in accordance with an exemplary embodiment.

There is also provided a cosmetic preparation comprising the hair conditioning spray treatment as disclosed herein in a transparent package suitable for dispensing the agent in the form of uniform, small droplets, in accordance with an exemplary embodiment.

As used herein, the term "about" refers to amounts, concentrations or values that are within about 10 percent of the expressed amount, concentration or value. Additionally, all provided concentration ranges are intended to include all possible concentration ranges contained within the provided range.

As noted above, in accordance with an exemplary embodiment, there is provided a hair conditioning spray treatment comprising a combination of at least two components selected from components (i), (ii) and (iii):

(i) at least one cationic guar derivative (ii) at least one dicarboxylic acid, or a salt or derivative thereof, and (iii) at least one cationic surfactant selected from an amidoamine, a permanent cationic amidoamine, and mixtures thereof.

In an embodiment, the hair conditioning spray treatment as contemplated herein comprises at least two of the components listed above, and in another embodiment comprises three of the components listed above, i.e. at least one cationic guar derivative, and at least one dicarboxylic acid, or a salt or derivative thereof, and at least one cationic surfactant selected from an amidoamine, a permanent cationic amidoamine, and mixtures thereof. Regardless of what combination of components is selected, the disclosure herein of preferred options for the components apply mutatis mutandis to every one of the combinations. Further, the skilled person would understand that each of the components may include a single ingredient falling within the definition of the component, or may comprise more than one ingredient, each of which independently falls within the definition of the component.

In one exemplary embodiment, the hair conditioning spray treatment is silicone-free. In the context of the present disclosure, "silicone-free" is taken to mean that the treatment is free from organosilicon compounds, in particular free from silicones, trisiloxanes, and silicone oils.

Such treatments provide hair that is treated with the spray treatment with unexpected application and conditioning benefits, particularly distribution, detangling of wet hair, feel of dry hair, feel of hair tips, shine, smoothing, suppleness and anti-frizz.

Component (i) in the composition is a cationic guar derivative or a mixture of different cationic guar derivatives. The guar component (i) may be selected from any suitable cationic guar that exhibits a care effect. Suitable ingredients falling within this component include Carboxymethyl Hydroxypropyl Guar, C18-22 Hydroxyalkyl Hydroxypropyl Guar, Cyamopsis Tetragonoloba (Guar) Gum, Guar Hydroxypropyltrimonium Chloride, Hydrolyzed Guar, Hydroxypropyl Guar, and Hydroxypropyl Guar Hydroxypropyltrimonium Chloride. In one embodiment, the guar is Guar Hydroxypropyltrimonium Chloride or a combination of Guar Hydroxypropyltrimonium Chloride together with one or more different cationic guar derivatives. In another embodiment, component (i) is Guar Hydroxypropyltrimonium Chloride (i.e. not in combination with other cationic guar derivatives).

In an exemplary embodiment, the treatment disclosed herein may contain a total amount of component (i) ranging from about 0.001% to about 3%, such as from about 0.01% to about 2%, relative to the total weight of the treatment. In an embodiment, the total amount of component (ii) ranges from about 0.05% to about 2%, for example, from about 0.05% to about 1%, relative to the total weight of the treatment.

Component (ii) in the composition is a dicarboxylic acid, or a salt or derivative thereof or a mixture of different dicarboxylic acids/salts/derivatives thereof. The dicarboxylic component (ii) may be selected from any suitable dicarboxylic component that exhibits a care effect. Suitable ingredients falling within this component include dicarboxylic acids having 2 to 10 carbon atoms. The or each dicarboxylic acid may be selected from oxalic acid, malonic acid, succinic acid, glutaric acid, adipic acid, pimelic acid, azelaic acid, maleic acid, fumaric acid, sorbic acid and mixtures thereof. In an embodiment, component (ii) is succinic acid together with one or more different dicarboxylic acids/salts/derivatives thereof. In another embodiment, component (ii) is succinic acid.

The treatment disclosed herein may contain a total amount of component (ii) ranging from about 0.01% to about 5%, such as from about 0.1% to about 4%, relative to the total weight of the treatment. In an exemplary embodiment, the total amount of component (ii) ranges from about 0.3% to about 3%, for example from about 0.5% to about 2%, relative to the total weight of the treatment.

Component (iii) in the composition is a cationic surfactant or a mixture of different cationic surfactants. The cationic surfactants are selected from amidoamines, permanent cationic amidoamines, and mixtures thereof. Thus, component (iii) may be one amidoamine or a mixture of different amidoamines. Component (iii) may alternatively be one permanent cationic amidoamine or a mixture of different permanent cationic amidoamines. Component (iii) may alternatively be one or more amidoamines in combination with one or more permanent cationic amidoamines.

When an amidoamine is present, it may be selected from one or more of Brassicamidopropyl dimethylamine, lauramidopropyl dimethylamine, myristamidopropyl dimethylamine, stearamidopropyl dimethylamine, cocamidopropyl dimethylamine, ricinolamidopropyl dimethylamine, isostearamidopropyl dimethylamine, oleamidopropyl dimethylamine, behenamidopropyl dimethylamine and palmamidopropyl dimethylamine, preferably Brassicamidopropyl dimethylamine.

When a permanent cationic amidoamine is present, it may be selected from one or more of bis-(Isostearoyl/Oleoyl Isopropyl) dimonium methosulfate, Cetrimonium Methosulfate, Distearoylethyl Hydroxyethylmonium Methosulfate, Quatemium-33, behenamidopropyl ethyldimonium ethosulfate, behenamidopropyl PG-dimonium chloride, oleamidopropyl ethyldimonium ethosulfate, oleamidopropyl PG-dimonium chloride, cocamidopropyl ethyldimonium ethosulfate, cocamidopropyltrimonium chloride, ricinoleamidopropylethyldimonium ethosulfate, rinoleamidopropyltrimonium chloride, ricinoleamidopropyltrimonium methosulfate, stearamidopropyl ethyldimonium ethosulfate, stearamidopropyl trimonium methosulfate, undecyleneamidopropyltrimonium methosulfate, lauramidopropyl PG-dimonium chloride, canolamidopropyl ethyldimonium ethosulfate, preferably Bis-(Isostearoyl/Oleoyl Isopropyl) Dimonium Methosulfate and/or Cetrimonium Methosulfate and/or Distearoylethyl Hydroxyethylmonium Methosulfate.

In an exemplary embodiment, component (iii) comprises brassicamidopropyl dimethylamine. In accordance with another exemplary embodiment, a suitable combination of ingredients falling within component (iii) is brassicamidopropyl dimethylamine, distearoylethyl hydroxyethylmonium methosulfate, and cetrimonium methosulfate. Component (iii) may also be a combination of brassicamidopropyl dimethylamine, bis-(isostearoyl/oleoyl isopropyl) dimonium methosulfate, distearoylethyl hydroxyethylmonium methosulfate, and cetrimonium methosulfate.

The treatment disclosed herein may contain a total amount of component (iii) ranging from about 0.01% to about 10%, such as from about 0.1% to about 8%, relative to the total weight of the treatment. In an exemplary embodiment, the total amount of component (iii) ranges from about 0.5% to about 5%, more preferably from about 0.5% to about 3%, relative to the total weight of the treatment.

In an exemplary embodiment, the hair conditioning spray treatment comprises guar hydroxypropyltrimonium chloride, succinic acid, and brassicamidopropyl dimethylamine. Optional additional cationic surfactants include distearoylethyl hydroxyethylmonium methosulfate and cetrimonium methosulfate.

In another exemplary embodiment, the hair conditioning spray treatment comprises succinic acid, bis-(isostearoyl/oleoyl isopropyl) dimonium methosulfate, and brassicamidopropyl dimethylamine. Optional additional cationic surfactants include distearoylethyl hydroxyethylmonium methosulfate and cetrimonium methosulfate.

In a further exemplary embodiment, the hair conditioning spray treatment suitably further comprises one or more fatty alcohols. The or each fatty alcohol may be selected from Arachidyl Alcohol, Behenyl Alcohol, Brassica Alcohol, C9-11 Alcohols, C10-16 Alcohols, C12-13 Alcohols, C12-15 Alcohols, C12-16 Alcohols, C14-15 Alcohols, C14-22 Alcohols, C20-22 Alcohols, Caprylyl Alcohol, Cetearyl Alcohol, Cetyl Alcohol, Coconut Alcohol, Decyl Alcohol, Hydrogenated Brassica Alcohol, Hydrogenated Jojoba Alcohol, Hydrogenated Rapeseed Alcohol, Hydrogenated Tallow Alcohol, Hydroxystearyl Alcohol, Jojoba Alcohol, Lauryl Alcohol, Myristyl Alcohol, Oleyl Alcohol, Olive Alcohol, Palm Alcohol, Palm Kernel Alcohol, Stearyl Alcohol, Tallow Alcohol, Tridecyl Alcohol, and mixtures thereof. In an exemplary embodiment, the fatty alcohol comprises or includes Cetearyl Alcohol; for example, includes Cetearyl Alcohol.

The treatment disclosed herein may contain a total amount of fatty alcohols ranging from about 0.1% to about 10%, such as from about 0.5% to about 5%, relative to the total weight of the treatment. In an embodiment, the total amount of fatty alcohols ranges from about 0.5% to about 3%, relative to the total weight of the treatment.

The hair conditioning spray treatment, in accordance with an embodiment, further comprises one or more further surfactants, i.e. a cationic, nonionic, amphoteric, or zwitterionic surfactant (any additional cationic surfactant being different to that required by component (iii)). Anionic surfactants may have a negatively charged hydrophilic end. Examples of anionic surfactants include sulfate, sulfonate, carboxylate, phosphate, or the like. Anionic surfactants may be sensitive to water hardness. Cationic surfactants may be those that have a positively charged hydrophilic end, such as a quaternary amine. Nonionic surfactants may have a hydrophilic end which may be charge neutral, such as an ethoxylate, glycoside, or poly-ol; such surfactants may not be sensitive to water hardness. Amphoteric surfactants may be those that have a hydrophilic end which has a functional group that is capable of acting as a base, and a functional group that is capable of acting as an acid, such as amine oxides. Zwitterionic surfactants may have both a positive and negative charge on their hydrophilic ends, such as sultaines, or betaines. The hydrophobic end may include a saturated or unsaturated, linear or branched, substituted or unsubstituted, cyclic or acyclic, alkyl or silyl chain containing at least 8 carbon or silicon atoms.

The hair conditioning spray treatment as contemplated herein further comprises one or more nonionic surfactants, in accordance with an embodiment. The or each nonionic surfactant suitably comprises or includes an ester of a fatty acid, in an exemplary embodiment. The or each nonionic surfactant may comprise or include, for example, Glycol Distearate.

The treatment disclosed herein may contain a total amount of nonionic surfactant ranging from about 0.1% to about 5%, such as from about 0.5% to about 3%, relative to the total weight of the treatment. In an embodiment, the total amount of nonionic surfactant ranges from about 0.5% to about 2.5%, relative to the total weight of the treatment.

The hair conditioning spray treatment in accordance with an embodiment further comprises one or more solubilizers. The or each solubilizer may be an ethoxylation product of optionally hardened vegetable and animal oils. The or each solubilizer may be ethoxylated mono-, di- and triglycerides of C8-22 fatty acids with 4 to 50 ethylene oxide units, for example hydrogenated ethoxylated castor oil, olive oil ethoxylate, almond oil ethoxylate, mink oil ethoxylate, polyoxyethylene glycol, caprylic/capric acid glycerides, polyoxyethylene glycerol monolaurate and polyoxyethylene glycol coconut fatty acid glycerides. For example, the solubilizer may comprise or include Caprylic/Capric Triglyceride.

The treatment disclosed herein may contain a total amount of solubilizers ranging from about 0.1% to about 5%, such as from about 0.5% to about 3%, relative to the total weight of the treatment. For example, the total amount of solubilizers ranges from about 0.5% to about 2.5%, relative to the total weight of the treatment.

In accordance with another exemplary embodiment, the hair conditioning spray treatment contemplated herein further comprises one or more further benefit agents. Suitable benefit agents are selected from moisturizing ingredients, conditioning ingredients, illuminating ingredients antidandruff agents, preservatives, UV filters, fats and oils, thickeners, polymers, humectants, vitamins and/or provitamins, hair structuring agents, hair care agents, hair restorers and agents for combating hair loss.

A moisturizing ingredient may be any component that is capable of moisturizing the hair, and may include occlusive-type moisturizers, oils, esters, humectants, and vitamins that may strengthen the hair to benefit the hair's natural moisture retention abilities.

A conditioning ingredient may be any component that is capable of improving the moisture or feel of the hair, and may include the aforementioned moisturizing ingredients, proteins, and hydrolyzed proteins.

Illuminating ingredients may be any component that provides a sparkling visual effect, and may include mica, pearlescent pigments, and glitter particles.

Oils are nonpolar substances that are viscous liquids at room temperature (from about 20-25° Celsius). Non-limiting examples of suitable oils include natural oils such as triglycerides and petroleum-derived hydrocarbons, synthetic oils such as hydrocarbons and silicones (if the treatment is silicone-free, any oil present is not a silicone oil), and semi-synthetic oils such as hydrogenated or chemically modified triglycerides.

Non-limiting examples of specific oils which may be used in a treatment contemplated herein include coconut oil, *Prunus armeniaca* Kernel Oil, palm oil, castor oil, meadowfoam seed oil, vegetable oil, animal fats such as tallow, hydrogenated analogs of the foregoing, paraffinum liquidum, and combinations and mixtures thereof.

The treatment disclosed herein may contain a total amount of oils ranging from about 0.01% to about 5%, such as from about 0.01% to about 3%, relative to the total weight of the treatment. For example, the total amount of oils ranges from about 0.1% to about 2%, relative to the total weight of the treatment.

Any ester-based moisturizing ingredient may be suitable for inclusion in a treatment as contemplated herein. There may be some overlap between ester-based moisturizing ingredients and oil-based moisturizing ingredients. Non-limiting examples of suitable ester-based moisturizing ingredients include monoesters and polyesters, including triglyceride oils. Non-limiting examples of specific oils which may be used in a treatment contemplated herein include acetylated glycol stearate, arachidyl behenate, butyl avocadate, butyl myristate, cetearyl palmate, coco-caprylate, decyl oleate, dipentaerythrityl hexahydroxystearate, ethyl oleate, isocetyl myristate, propylene glycol stearate, diisopropyl adipate, polysorbates, and combinations and mixtures thereof.

Any humectant may be suitable for inclusion in a treatment contemplated herein. Humectants are hygroscopic substances that attract ambient moisture. Non-limiting examples of suitable humectants include glycerol, acetyl arginine, betaine, lauryl malamide, mannitol, propylene glycol, xylose, polymeric humectants such as lauryl methyl gluceth-10 hydroxypropyldimonium chloride, and combinations and mixtures thereof.

Any vitamins that strengthen the hair, whereby benefiting the hair's natural moisture retention abilities, may be suitable for inclusion in a treatment as contemplated herein. Other vitamins that may be suitable are those that modulate hair rejuvenation or growth. For example, suitable vitamins include retinol (vitamin A), thiamine (vitamin B1), riboflavin (vitamin B2), niacin (vitamin B3), pantothenic acid (vitamin B5), pyridoxine (vitamin B6), biotin (vitamin B7), folic acid (vitamin B9), cyanocobalamin (vitamin B12), ascorbic acid (vitamin C), tocopherol (vitamin E), and combinations and derivatives thereof.

Any proteins that provide a conditioning effect to the hair, whereby benefiting the hair's appearance or feel, may be suitable for inclusion in a treatment as contemplated herein. Proteins are natural polymers produced by cellular machinery; proteins are amino acid chains held together through amide bonds, and may include crosslinks, secondary, and/or tertiary structure as a result of the amino acids present, and the order of the amino acids in the protein. Proteins may also be modified, such as by attachment of sugars (glycosylation); such modification may occur enzymatically or chemically. Non-limiting examples of proteins include keratin, silk, wheat protein, glycoprotein, lactabumin, soy protein, collagen, and combinations thereof.

Any hydrolyzed protein that provides a conditioning effect to hair may be suitable for inclusion in a treatment as contemplated herein. Hydrolyzed proteins are protein chains that have been cleaved along the amide backbone; hydrolysis may be enzymatic, acid-catalyzed, or base-catalyzed. Non-limiting examples of suitable hydrolyzed proteins include hydrolysis products of the above proteins.

Any mica that is capable of providing an optical effect may be suitable for inclusion in a treatment as contemplated herein. Micas are a class of phyllosilicate minerals. Non-limiting examples of micas include muscovite, biotite, leipdolite, phlogopite, zinnwaldite, clintonite, illite, phengite, and combinations thereof.

Any pearlescent pigment that is capable of providing an optical effect on the hair may be suitable for inclusion in a treatment as contemplated herein. Pearlescent pigments are particulate pigments that have a shiny or glossy appearance. In some examples, pearlescent pigments provide different colors based on the angle of incident light and the angle of observation. Non-limiting examples of pearlescent pigments include mica coated with metal oxides, aluminum oxide coated with metal oxides, bismuth oxychloride, and combinations thereof.

Any glitter particles that are capable of providing an optical effect on the hair may be suitable for inclusion in a treatment as contemplated herein. Glitter may be flat particles that reflect light at different angles, causing the particles to shimmer. Non-limiting examples of glitter particles include plastic-based glitters, glitter derived from stones such as malachite, glitter derived from natural sources such as insect-based glitters and glass-based glitters.

The hair conditioning spray treatment as contemplated herein may also include additional components. Such additional components may include a suspending polymer, a wax, a preservative, a fragrance, a deposition aid, and combinations thereof. The treatment may also contain additives known to an individual skilled in the art, such as a dye, a pigment, an antibacterial agent, a foaming agent, a plant extract, plant matter, a chelator, an alkali metal halide, and combinations thereof.

A wax is a hydrophobic solid that is malleable at or near room temperature (from about 20-25° Celsius). A wax may be included in a treatment as contemplated herein as a carrier, viscosity modifier, hair styling agent, or adjuvant. A wax may be capable of shaping the hair, as well as acting as a moisturizing ingredient or conditioner due to its hydrophobic nature. Non-limiting examples of types of waxes include esters of fatty alcohols with fatty acids, sterol esters, and hydrocarbons. Non-limiting examples of waxes include beeswax, lanolin, sunflower seed wax, carnauba wax, montan wax, candelilla wax, paraffin wax, tallow tree wax, ceresin wax, and derivatives and combinations thereof.

Preservatives are compounds that may be added to the treatment contemplated herein to prevent undesirable decomposition over time. Non-limiting examples of preservatives include benzoic acid, benzyl alcohol, phenol, phenoxyethanol, formaldehyde, glyoxal, DMDM hydantoin, cresol, para-hydroxybenzoic acid and esters thereof, chlorhexidine, propionic acid, and salts and/or combinations thereof. The treatment contemplated herein may contain up to about 5% by weight of preservatives, relative to the total weight of the treatment. For example, the treatment contemplated herein may contain from about 0.01% to about 3%, such as from about 0.05% to about 2% of preservatives, relative to the total weight of the treatment.

A fragrance comprises a number of ingredients; fragrance ingredients are compounds that provide the composition with a pleasing scent. While fragrances may often be complex mixtures of fragrance ingredients, it is also possible to include a single fragrance ingredient in a composition. The olfactory intensity of a fragrance ingredient may be a function of the concentration of the fragrance ingredient, the vapor pressure of the fragrance ingredient, and the potency of the interactions between the fragrance ingredient and a user's olfactory receptors. A fragrance may be incorporated into the treatment contemplated herein along with the benefit agent in order to provide a user with a sensory awareness that the moisturizing ingredient has been deployed onto the hair. Alternatively, a fragrance may also be incorporated into the treatment contemplated herein directly. Fragrance ingredients are generally known by an individual skilled in the art, and include ketones, aldehydes, esters, and the like. Fragrance ingredients also include naturally-occurring plant and animal oils. Non-limiting examples of suitable fragrance ingredients include linalool, hexyl salicylate, citronellol, butylphenyl methylpropional, limonene, allylanisole, carvone, nonalactone, liffarome, 2,4-dimethyl-3-cyclohexene carboxaldehyde, adoxal, galaxolide, methyl benzoate, geraniol, camphor, citral, eucalyptol, alpha-damascone, florhydral, and the like. Derivatives and combinations thereof may also be suitable for inclusion.

The treatment as contemplated herein may contain a fragrance in an amount of up to about 10% by weight, such as from about 0.001% to about 5% by weight, relative to the weight of the total treatment. For example, the treatment as contemplated herein may contain a fragrance in an amount of from about 0.01% to about 4% by weight, or from about 0.05% to about 2% by weight, relative to the total weight of the treatment.

Dyes and pigments are compounds which confer color to a composition or to the hair to which a dye or pigment is applied. Dyes and pigments may be added to the treatment contemplated herein in order to imbue the composition with a consumer-acceptable color. In another example, a dye or pigment is added to the treatment contemplated herein in order to provide a simultaneous coloring effect to the hair. Non-limiting examples of dyes and pigments which may be used to color the treatment contemplated herein include titanium dioxide, mica, iron oxides, violet 2, red 4, red 6, red 7, red 33, red 40, blue 1, blue 4, yellow 5, yellow 6, yellow 10, orange 4, orange 5, orange 10, vat red 1, vat blue 1, vat blue 4, vat blue 6, vat orange 7, vat violet 2, and combinations thereof.

Dyes and pigments may also include permanent dyes, and direct dyes, which may be either semi-permanent dyes or temporary dyes. Permanent dyes may include oxidative dye precursors, which react with oxidizing agents, such as hydrogen peroxide, to form dye molecules on the hair. Oxidative dye precursors include oxidation bases, which include para- and ortho-substituted aromatic rings; these may be supplemented by couplers, which modify the color produced by the oxidation dye precursors, and include meta-substituted aromatic rings. Semi-permanent dyes include anthraquinones, other multicyclic ring systems, as well as monocyclic compounds that confer color directly, such as 4-amino-3-nitrophenol. Temporary hair dyes confer color to the hair only until the hair is washed, and include inorganic pigments comprising titanium dioxide, mica, iron oxides, and/or ultramarines, as well as cationic dyes such as basic blue 99 and basic brown 17. Dyes and pigments may be used in any suitable quantity, including up to about 20% by weight, relative to the total weight of the treatment. For example, a treatment contemplated herein may contain from about 1% to about 20% by weight, such as from about 4% to about 15% by weight of dyes and/or pigments, relative to the total weight of the treatment. In one example in which the treatment contains a number of permanent dyes, the treatment may also be mixed with another composition containing from about 2% to about 30% by weight, such as from about 6% to about 20% of an oxidant, such as hydrogen peroxide.

A treatment contemplated herein may also include at least one antibacterial agent. An antibacterial agent is any agent that assists in the removal of bacteria, kills bacteria, or arrests bacterial growth. Some antibacterial agents also have additional functions, and belong to one or more than one of the aforementioned or following classes. Suitable non-limiting examples of antibacterial agents include antiseptics, triclosan, triclocarban, usnic acid salts, benzethonium salts, benzalkonium salts, compounds which inhibit the 70S (bacterial) ribosome, and compounds which reduce the integrity of the bacterial cell wall. Additional non-limiting examples of antibacterial agents include ethanol, isopropanol, aminoglycosides (such as neomycin), cephalosporins (such as cefalexin), lincosamides (such as lincomycin), tetracyclines (such as doxycycline), penicillins (such as amoxicillin), and combinations thereof. A treatment as contemplated herein may contain an antibacterial agent in any appropriate amount, such as from about 0.1% to about 75% by weight. Antibacterial agents such as ethanol and isopropanol may require higher concentrations, such as from about 50% to about 75%, and may also provide the carrier for the treatment contemplated herein. In contrast, antibacterial active ingredients such as benzethonium and benzalkonium salts may be effective at lower concentrations, such as from about 0.1% to about 10% by weight, or from about 1% to about 6% by weight, relative to the total weight of the treatment.

Foaming agents are compounds that stabilize foams. Foaming agents increase the propensity of a composition to form a foam, and/or may stabilize a foam by inhibiting the coalescence of bubbles within the foam. Certain types of surfactants are capable of acting as foaming agents in the treatment contemplated herein; however, not every type of surfactant enhances foam stability. Non-limiting examples of foaming agents include sodium laureth sulfate, cocamidopropyl betaine, cocamidopropyl hydroxysultaine, behenyl betaine, hydroxystearamide MEA, lauramide MEA, myristamide MEA, myristamide DEA, PEG-3 lauramide, PEG-2 lauramine, lauramine oxide, PEG-3 lauramine oxide, and cocamine oxide. A number of foaming agents may be included the treatment contemplated herein at concentrations up to about 10% by weight, such as from about 0.1% to about 7% by weight, or from about 0.5% to about 5% by weight, relative to the total weight of the treatment.

Plant extracts are natural compounds or mixtures of compounds produced in a plant that contain at least one agent that has either a real or perceived benefit to the skin, or to the composition as a whole. The inclusion of some plant extracts may improve consumer acceptance of a composition on the basis of these benefits, or a consumer preference for naturally produced compositions over synthetically produced compositions. Plant extracts include oils, fragrance ingredients, fatty acids, and/or various other components depending on the extraction methods employed and any subsequent processing that is performed. Non-limiting examples of plant extracts include *Prunus amygdalus* dulcis extract, Oenothera biennis extract, Zingiber officinale extract, Jasminum extracts, *Lavandula angustifolia* extract, Menthapiperita extract, Rosa extracts, *Hypericum perforatum* extract, and combinations thereof. The treatment contemplated herein may contain up to about 20% by weight, such as from about 0.1% to about 15% by weight, or from about 0.5% to about 10% by weight of plant extracts, relative to the total weight of the treatment.

Plant matter is plant material which may be incorporated into the treatment as contemplated herein. Such plant material may provide abrasive properties as exfoliants, fragrance properties, or may be able to act as a thickener. The incorporation of plant matter into a composition may improve consumer acceptance, which may be based on the perception of the natural qualities of the compositions including plant matter. Non-limiting examples of plant matter which may be incorporated in a treatment as contemplated herein include whole flowers, flower petals, stems, seeds, roots, and fruits.

Chelators are compounds that coordinate metal ions. Chelators may be included in a treatment as contemplated herein as antibacterial agents, preservatives, pH regulators, or to provide other such properties to the composition. Non-limiting examples of chelators include natural polyacids (such as citric acid), phosphate salts (such as disodium pyrophosphate), bisphosphonates (such as etidronic acid), aminocarboxylic acids (such as ethylenediaminetetraacetic acid (EDTA) and ethylenediamine-N,N'-disuccinic acid (EDDS)), and combinations and/or salts thereof. Chelators may be included in the treatment disclosed herein in any suitable amount, such as up to about 5% by weight, relative to the total weight of the treatment.

Alkali metal halides are salts of alkali metals and halogen atoms. Alkali metal halides may be included in a treatment as contemplated herein as thickeners, ionic strength modulators, or to confer other such properties to the treatment. Alkali metal halides are neutral compounds. Non-limiting examples of alkali metal halides include lithium chloride, lithium bromide, sodium chloride, sodium bromide, potassium chloride, potassium bromide, and combinations thereof. The treatment contemplated herein may contain an alkali metal halide in any suitable amount, such as up to about 5% by weight, relative to the total weight of the treatment.

The treatment contemplated herein may also contain other, additional components known to an individual skilled in the art. For example, the treatment contemplated herein may contain additional polymers, which may be natural, synthetic, and/or semi-synthetic. Natural polymers include hydrolyzed keratin, silk, collagen, honey, cellulose, and the like. Synthetic polymers include acrylates/acrylamide copolymers, acrylamidopropyltrimonium chloride/acrylates copolymers, polyethylene glycol polymers, polypropylene glycol polymers, polyquaterniums, and the like. Semi-synthetic polymers include chemically modified natural polymers, polymers assembled from both natural and synthetic monomers, and the like. In another example, the treatment disclosed herein includes an exfoliant, which are particles that do not dissolve in the carrier and act as an abrasive to assist in efficient cleansing of the hair. In a further example, the treatment contemplated herein includes a pH buffer, to maintain the pH within a desired range. In another example, the treatment contemplated herein includes a pH adjusting agent, which may be provided either with or without a pH buffer. In yet another example, the treatment contemplated herein includes an enzyme. In a further example, the treatment contemplated herein may contain a UV stabilizer or protectant which may reduce damage to the hair resulting from exposure to the sun. In another example, the treatment contemplated herein may contain a bleaching agent.

The treatment contemplated herein may have any viscosity that renders it suitable for application as a spray. Viscosity of the treatment disclosed herein may be measured in centipoise (cps). The treatment disclosed herein may have a viscosity in the range of about 0.8 cps to about 500,000 cps. In one example, a treatment as disclosed herein is not subjected to a foaming operation upon dispensing, and is offered as a sprayable liquid with a viscosity in the range of about 1,000 to about 5,000 cps, such as from about 2,000 cps to about 4,000 cps.

Methods

In another exemplary embodiment, a method for conditioning hair using a spray treatment as contemplated herein is provided. The method includes applying the hair conditioning spray treatment as contemplated herein to the hair. The method includes spraying the hair conditioning spray treatment as contemplated herein onto the hair. The method may additionally include touching or rubbing the hair.

The method for conditioning hair using a hair conditioning spray treatment as contemplated herein may also include additional, optional steps. In one example, such steps may include air drying the hair, drying the hair using heat, styling the hair, and any other suitable step that is known to an individual skilled in the art of hair treatment.

Various exemplary embodiments disclosed herein may be defined by the following numbered statements.

1. A hair conditioning spray treatment comprising at least two components selected from components (i), (ii) and (iii):
   (i) at least one cationic guar derivative
   (ii) at least one dicarboxylic acid, or a salt or derivative thereof, and
   (iii) at least one cationic surfactant selected from an amidoamine, a permanent cationic amidoamine, and mixtures thereof.
2. A hair conditioning spray treatment according to statement 1, comprising
   (i) at least one cationic guar derivative, and
   (ii) at least one dicarboxylic acid, or a salt or derivative thereof.
3. A hair conditioning spray treatment according to statement 1, comprising
   (i) at least one cationic guar derivative, and
   (iii) at least one cationic surfactant selected from an amidoamine, a permanent cationic amidoamine, and mixtures thereof.
4. A hair conditioning spray treatment according to statement 1, comprising
   (ii) at least one dicarboxylic acid, or a salt or derivative thereof, and
   (iii) at least one cationic surfactant selected from an amidoamine, a permanent cationic amidoamine, and mixtures thereof.
5. A hair conditioning spray treatment according to any preceding statement, comprising:
   (i) at least one cationic guar derivative, and
   (ii) at least one dicarboxylic acid, or a salt or derivative thereof, and
   (iii) at least one cationic surfactant selected from an amidoamine, a permanent cationic amidoamine, and mixtures thereof.
6. A hair conditioning spray treatment according to any preceding statement, wherein the or each cationic guar derivative is selected from Carboxymethyl Hydroxypropyl Guar, C18-22 Hydroxyalkyl Hydroxypropyl Guar, Cyamopsis Tetragonoloba (Guar) Gum, Guar Hydroxypropyltrimonium Chloride, Hydrolyzed Guar, Hydroxypropyl Guar, and Hydroxypropyl Guar Hydroxypropyltrimonium Chloride.
7. A hair conditioning spray treatment according to any preceding statement, wherein component (i) comprises or includes Guar Hydroxypropyltrimonium Chloride.
8. A hair conditioning spray treatment according to any preceding statement, wherein component (i) is present in a total amount ranging from about 0.001% to about 3%, relative to the total weight of the treatment.
9. A hair conditioning spray treatment according to any preceding statement, wherein component (i) is present in a total amount ranging from about 0.01% to about 2%, relative to the total weight of the treatment.
10. A hair conditioning spray treatment according to any preceding statement, wherein component (i) is present in a total amount ranging from about 0.05% to about 2%, preferably from about 0.05% to about 1%, relative to the total weight of the treatment.
11. A hair conditioning spray treatment according to any preceding statement, wherein the or each dicarboxylic acid has 2 to 10 carbon atoms.
12. A hair conditioning spray treatment according to any preceding statement, wherein the or each dicarboxylic acid is selected from oxalic acid, malonic acid, succinic acid, glutaric acid, adipic acid, pimelic acid, azelaic acid, maleic acid, fumaric acid, sorbic acid and mixtures thereof.
13. A hair conditioning spray treatment according to any preceding statement, wherein component (ii) comprises or includes succinic acid.
14. A hair conditioning spray treatment according to any preceding statement, wherein component (ii) is present in an amount ranging from about 0.01% to about 5%, relative to the total weight of the treatment.
15. A hair conditioning spray treatment according to any preceding statement, wherein component (ii) is present in an amount ranging from about 0.1% to about 4%, relative to the total weight of the treatment.
16. A hair conditioning spray treatment according to any preceding statement, wherein component (ii) is present in an amount ranging from about 0.3% to about 3%, preferably from about 0.5% to about 2%, relative to the total weight of the treatment.
17. A hair conditioning spray treatment according to any preceding statement, wherein component (iii) comprises at least one amidoamine (iiia).
18. A hair conditioning spray treatment according to any preceding statement, wherein component (iii) comprises at least one permanent cationic amidoamine (iiib).
19. A hair conditioning spray treatment according to any preceding statement, wherein component (iii) comprises a mixture of at least one amidoamine and at least one permanent cationic amidoamine (iiic).
20. A hair conditioning spray treatment according to any preceding statement, wherein the or each amidoamine is selected from Brassicamidopropyl dimethylamine, lauramidopropyl dimethylamine, myristamidopropyl dimethylamine, stearamidopropyl dimethylamine, cocamidopropyl dimethylamine, ricinolamidopropyl dimethylamine, isostearamidopropyl dimethylamine, oleamidopropyl dimethylamine, behenamidopropyl dimethylamine and palmamidopropyl dimethylamine.
21. A hair conditioning spray treatment according to any preceding statement, wherein component (iii) comprises or includes Brassicamidopropyl Dimethylamine.
22. A hair conditioning spray treatment according to any one of statements 18 to 20, wherein the or each permanent cationic amidoamine is selected from bis-(Isostearoyl/Oleoyl Isopropyl) dimonium methosulfate, Cetrimonium Methosulfate, Quaternium-33, behenamidopropyl ethyldimonium ethosulfate, behenamidopropyl PG-dimonium chloride, oleamidopropyl ethyldimonium ethosulfate, oleamidopropyl PG-dimonium chloride, cocamidopropyl ethyldimonium ethosulfate, cocamidopropyltrimonium chloride, ricinoleamidopropylethyldimonium ethosulfate, rinoleamidopropyltrimonium chloride, ricinoleamidopropyltrimonium methosulfate, stearamidopropyl ethyldimonium ethosulfate, stearamidopropyl trimonium methosulfate, undecyleneamidopropyltrimonium methosulfate, lauramidopropyl PG-dimonium chloride, canolamidopropyl ethyldimonium ethosulfate, and mixtures thereof.
23. A hair conditioning spray treatment according to any preceding statement, wherein component (iii) comprises or includes bis-(Isostearoyl/Oleoyl Isopropyl) dimonium methosulfate.
24. A hair conditioning spray treatment according to any preceding statement, wherein component (iii) comprises or includes a mixture of Brassicamidopropyl Dimethylamine, Bis-(Isostearoyl/Oleoyl Isopropyl) Dimonium Methosulfate.

25. A hair conditioning spray treatment according to any preceding statement, wherein component (iii) comprises or includes a mixture of Brassicamidopropyl Dimethylamine, and Bis-(Isostearoyl/Oleoyl Isopropyl) Dimonium Methosulfate and Cetrimonium Methosulfate.
26. A hair conditioning spray treatment according to any preceding statement, wherein component (iii) is present in a total amount ranging from about 0.01% to about 10%, relative to the weight of the treatment.
27. A hair conditioning spray treatment according to any preceding statement, wherein component (iii) is present in a total amount ranging from about 0.1% to about 8%, relative to the total weight of the treatment.
28. A hair conditioning spray treatment according to any preceding statement, wherein component (iii) is present in a total amount ranging from about 0.5% to about 5%, preferably from about 0.5% to about 3%, relative to the total weight of the treatment.
29. A hair conditioning spray treatment according to statement 1, comprising Guar Hydroxypropyltrimonium Chloride, Succinic Acid, and Brassicamidopropyl Dimethylamine.
30. A hair conditioning spray treatment according to statement 1, comprising Succinic Acid, Brassicamidopropyl Dimethylamine and Bis-(Isostearoyl/Oleoyl Isopropyl) Dimonium Methosulfate.
31. A hair conditioning spray treatment according to any preceding statement, further comprising one or more fatty alcohol.
32. A hair conditioning spray treatment according to statement 31, wherein the or each fatty alcohol is selected from Arachidyl Alcohol, Behenyl Alcohol, Brassica Alcohol, C9-11 Alcohols, C10-16 Alcohols, C12-13 Alcohols, C12-15 Alcohols, C12-16 Alcohols, C14-15 Alcohols, C14-22 Alcohols, C20-22 Alcohols, Caprylyl Alcohol, Cetearyl Alcohol, Cetyl Alcohol, Coconut Alcohol, Decyl Alcohol, Hydrogenated Brassica Alcohol, Hydrogenated Jojoba Alcohol, Hydrogenated Rapeseed Alcohol, Hydrogenated Tallow Alcohol, Hydroxystearyl Alcohol, Jojoba Alcohol, Lauryl Alcohol, Myristyl Alcohol, Oleyl Alcohol, Olive Alcohol, Palm Alcohol, Palm Kernel Alcohol, Stearyl Alcohol, Tallow Alcohol, Tridecyl Alcohol, and mixtures thereof.
33. A hair conditioning spray treatment according to statement 31 or 32, wherein the or each fatty alcohol comprises or includes Cetearyl Alcohol.
34. A hair conditioning spray treatment according to any preceding statement, further comprising one or more nonionic surfactants.
35. A hair conditioning spray treatment according to statement 34, wherein the or each nonionic surfactant comprises or includes an ester of a fatty acid.
36. A hair conditioning spray treatment according to statement 34 or 35, wherein the or each nonionic surfactant comprises or includes Glycol Distearate.
37. A hair conditioning spray treatment according to any preceding statement, further comprising one or more benefit agents.
38. A hair conditioning spray treatment according to statement 37, wherein the or each benefit agent is selected from moisturizing ingredients, conditioning ingredients, illuminating ingredients, antidandruff agents, preservatives, UV filters, fats and oils, thickeners, polymers, humectants, vitamins and/or provitamins, hair structuring agents, hair care agents, hair restorers and agents for combating hair loss.
39. A hair conditioning spray treatment according to statement 37 or 38, wherein the benefit agents are selected protein hydrolysates, fats and oils, vitamins, amino acids and/or the derivatives thereof, plant extracts, cationic polymers and hair structuring agents.
40. A hair conditioning spray treatment according to statement 37, 38 or 39, wherein the benefit agent comprises one or more vegetable, animal, mineral and synthetic oils.
41. A hair conditioning spray treatment according to statement 40, wherein the or each oil is a nut, seed or kernel oil.
42. A hair conditioning spray treatment according to statement 41, wherein the oil is *Prunus armeniaca* Kernel Oil.
43. A hair conditioning spray treatment according to any preceding statement, wherein the benefit agent comprises Quaternium-91.
44. A hair conditioning spray treatment according to any preceding statement, further comprising one or more solubilizers.
45. A hair conditioning spray treatment according to statement 44, wherein the or each solubilizer is an ethoxylation product of optionally hardened vegetable and animal oils.
46. A hair conditioning spray treatment according to statement 44 or 45, wherein the or each solubilizer is ethoxylated mono-, di- and triglycerides of C8-22 fatty acids with 4 to 50 ethylene oxide units, for example hydrogenated ethoxylated castor oil, olive oil ethoxylate, almond oil ethoxylate, mink oil ethoxylate, polyoxyethylene glycol, caprylic/capric acid glycerides, polyoxyethylene glycerol monolaurate and polyoxyethylene glycol coconut fatty acid glycerides.
47. A hair conditioning spray treatment according to statement 46, wherein the solubilizer comprises or includes Caprylic/Capric Triglyceride.
48. A hair conditioning spray treatment according to any preceding statement, which is free of silicones.
49. A method of conditioning keratin fibers, comprising contacting a keratin fiber with a conditioning-effective amount of the hair conditioning spray treatment of any preceding statement.
50. A method of conditioning keratin fibers, comprising contacting a plurality of keratin fibers with an amount of the hair conditioning spray treatment of any one of statements 1 to 48 effective to increase the volume of the keratin fibers on styling.
51. A method for conditioning keratin fibers, wherein the hair conditioning spray treatment of any one of statements 1 to 48 is spray-applied onto wet or dry keratin fibers and left on the keratin fibers until they are next washed.
52. A cosmetic preparation comprising the hair conditioning spray treatment of any one of statements 1 to 48 in a transparent package suitable for dispensing the agent in the form of uniform, small droplets.

EXAMPLES

The following formulation was tested and compared with the marketed product GK Supreme Length, available from Henkel.

TABLE 1

| Inventive formulation | |
| --- | --- |
| Ingredient (INCI name) | wt % |
| Aqua | |
| Caprylic/Capric Triglyceride | 2.00 |
| Glycol Distearate | 2.00 |
| Distearoylethyl Hydroxyethylmonium Methosulfate | 1.00 |
| Brassicamidopropyl Dimethylamine | 1.00 |

TABLE 1-continued

Inventive formulation

| Ingredient (INCI name) | wt % |
|---|---|
| Glycerin | 1.00 |
| Phenoxyethanol | 1.00 |
| Cetearyl Alcohol | 0.80 |
| Succinic Acid | 0.70 |
| Cetearyl Alcohol | 0.50 |
| Quaternium-91 | 0.45 |
| Cetearyl Alcohol | 0.30 |
| Parfum | 0.30 |
| Cetrimonium Methosulfate | 0.25 |
| Prunus Armeniaca Kernel Oil | 0.20 |
| Panthenol | 0.10 |
| Ethylhexylglycerin | 0.10 |
| Guar Hydroxypropyltrimonium Chloride | 0.09 |
| Pantolactone | 0.002 |
| Aqua | Q.S. |

The GK Supreme Length treatment spray comprises (amongst other ingredients) Polyquaternium-16 (a polymeric quaternary ammonium salt formed from methylvinylimidazolium chloride and vinylpyrrolidone), cetrimonium chloride, lactic acid, trideceth-5, Alcohol, Glycerin, *Paeonia lactiflora* Root Extract, Hydrolyzed Keratin, *Prunus armeniaca* Kernel Oil and Tocopheryl Acetate.

The products tested were treatment products and were tested on wet hair. 1.7 g of the inventive composition was tested, and 2 g of the GK Supreme Length treatment spray was tested. The hair characteristics of the model were as follows:

TABLE 2

Hair characteristics

| natural color | hair condition | hair type | hair length | hair density | hair diameter | scalp condition |
|---|---|---|---|---|---|---|
| 5-/ Medium Brown | highly porous | bleached, straight, frizzy | medium 12-25 cm | medium | fine | normal |

TABLE 3

Test results

| | GK Supreme Length | Contemplated Spray Treatment |
|---|---|---|
| Consistency | 5 | 5 |
| Distribution | 4 | 5* |
| Smell | 5 | 5 |
| Detangling of wet hair | 3 | 4 |
| Combability of wet hair | 5 | 5 |
| Feel of wet hair | 4 | 4 |
| Blow drying | 5 | 5 |
| Ease of styling | 5 | 5 |
| Drying time | 5 | 5 |
| Combability of dry hair | 5 | 5 |
| Feel of dry hair | 4 | 5 |
| Feel of hair tips | 3 | 4 |
| Static control | 5 | 5 |
| Shine | 4 | 5 |
| Bounce | 4 | 4 |
| Smoothing | 4 | 5 |
| Suppleness | 4 | 5 |

TABLE 3-continued

Test results

| | GK Supreme Length | Contemplated Spray Treatment |
|---|---|---|
| Anti-Frizz | 4 | 5 |
| Moisture | 5 | 5 |
| Overburdening | 5 | 5 |
| Overall assessment | 4 | 5 |
| Proband Opinion | 4 | 5 |

*A lower quantity of the inventive spray treatment was required

Thus, while both products performed well, it can be seen that the hair spray treatment contemplated herein achieved comparable properties compared to the marketed product in many respects, and improved properties in terms of distribution, detangling of wet hair, feel of dry hair, feel of hair tips, shine, smoothing, suppleness, anti-frizz, and overall assessment.

It will be appreciated that the exemplary embodiments may be modified within the scope of the appended claims.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair conditioning spray treatment consisting of:
   (i) guar hydroxypropyltrimonium chloride in an amount of from about 0.001% to about 3%, relative to the total weight of the treatment,
   (ii) succinic acid in an amount of from about 0.01% to about 5%, relative to the total weight of the treatment,
   (iii) brassicamidopropyl dimethylamine in an amount of from about 0.01% to about 10%, relative to the total weight of the treatment,
   (iv) water,
   (v) caprylic/capric triglyceride,
   and optionally one or more additional components selected from the group of:
   (vi) glycol distearate,
   (vii) distearoylethyl hydroxyethylmonium methosulfate,
   (viii) glycerin,
   (ix) phenoxyethanol,
   (x) cetearyl alcohol,
   (xi) quaternium-91,
   (xii) parfum,
   (xiii) cetrimonium methosulfate,
   (xiv) *Prunus armeniaca* kernel oil,
   (xv) panthenol,
   (xvi) ethylhexylglycerin, and
   (xvii) pantolactone.

* * * * *